United States Patent
Ristol Debart et al.

(10) Patent No.: US 9,200,032 B2
(45) Date of Patent: Dec. 1, 2015

(54) PROCESS FOR OBTAINING AN IGG COMPOSITION THROUGH HEAT TREATMENT

(71) Applicant: Grifols, S.A., Barcelona (ES)

(72) Inventors: Pere Ristol Debart, Barcelona (ES); Salvador Grancha Gamon, Barcelona (ES)

(73) Assignee: GRIFOLS, S.A., Barcelona (ES)

(*) Notice: Subject to any disclaimer, the term of this patent is extended or adjusted under 35 U.S.C. 154(b) by 225 days.

(21) Appl. No.: 13/838,424

(22) Filed: Mar. 15, 2013

(65) Prior Publication Data

US 2014/0113355 A1    Apr. 24, 2014

(30) Foreign Application Priority Data

Mar. 20, 2012 (ES) .................................. 201230413

(51) Int. Cl.
| | |
|---|---|
| A61K 39/395 | (2006.01) |
| C07K 16/06 | (2006.01) |
| C07K 19/00 | (2006.01) |
| C07K 1/18 | (2006.01) |
| C07K 1/36 | (2006.01) |

(52) U.S. Cl.
CPC .............. *C07K 1/36* (2013.01); *A61K 39/39525* (2013.01); *A61K 39/39591* (2013.01); *C07K 1/18* (2013.01); *C07K 16/065* (2013.01); *C07K 2317/21* (2013.01)

(58) Field of Classification Search
None
See application file for complete search history.

(56) References Cited

U.S. PATENT DOCUMENTS

| | | | |
|---|---|---|---|
| 514,375 | A | 2/1894 | Miller |
| 4,093,606 | A | 6/1978 | Coval |
| 4,165,370 | A | 8/1979 | Coval |
| 4,396,608 | A | 8/1983 | Tenold et al. |
| 4,540,573 | A | 9/1985 | Neurath et al. |
| 4,876,241 | A * | 10/1989 | Feldman et al. ............ 424/94.1 |
| 6,338,849 | B1 | 1/2002 | Chen et al. |
| 8,709,492 | B2 * | 4/2014 | Teschner et al. ............ 424/530 |
| 2001/0051708 | A1 * | 12/2001 | Laursen et al. ............ 530/387.1 |
| 2009/0068326 | A1 * | 3/2009 | Etzel et al. ............ 426/271 |
| 2010/0311952 | A1 * | 12/2010 | Falkenstein et al. ....... 530/387.1 |
| 2011/0293598 | A1 * | 12/2011 | Bruckschwaiger et al. ........... 424/130.1 |

FOREIGN PATENT DOCUMENTS

| | | |
|---|---|---|
| EP | 0196761 A2 | 10/1986 |
| EP | 0246579 B1 | 11/1987 |
| EP | 0253313 B1 | 1/1988 |
| EP | 0278422 B1 | 8/1988 |
| EP | 1225180 B1 | 7/2002 |
| EP | 0893450 B1 | 5/2004 |
| ES | 8206184 | 10/1981 |
| ES | 8201827 A1 | 4/1982 |
| ES | 2091161 A1 | 10/1996 |
| ES | 2091161 A1 | 10/1996 |
| ES | 2229784 T3 | 4/2005 |
| WO | WO 99/64462 | 12/1999 |

OTHER PUBLICATIONS

Liu et al. "Recovery and purification process development for monoclonal antibody production", mAbs 2:5, 480-499; Sep./Oct. 2010.*

European Search Report dated Jun. 3, 2013 in corresponding European Application No. 13158552.3.

Barandun, S. et al. "Intravenous administration of human γ-globulin". Vox Sang. 7: 157-174, 1962.

Cohn, E.J. et al. "Separation into Fractions of the Protein and Lipoprotein Components". J. Am. Chem. Soc. 1946; 68: 459-475.

Cramer, M. et al. "Stability over 36 months of a new liquid 10% polyclonal immunoglobulin product (IgPro10, Privigen®) stabilised with L-proline", Vox Sang. 2009. DOI: 10.1111/j.1423-0410.2008.01143.x.

Espanol, T. "Primary immunodeficiencies". Pharmaceutical Policy and Law 2009; 11(4): 277-283.

Eur.Ph. Monograph 6.3; and CMP Core SPC for normal immunoglobulin for intravenous administration: CPMP/BPWG/859/95 rev.2.

Hooper, J.A. "Intravenous immunoglobulins: evolution of commercial IVIG preparations". Immunol Allergy Clin. North Am. 2008; 28(4): 765-778.

Jolles, S. et al. "Clinical uses of intravenous immunoglobulin". Clin. Exp. Immunol. Oct. 2005; 142(1): 1-11.

Katakam, M. et al. "Aggregation of proteins and its prevention by carbohydrate excipients: Albumins and globulin". J. Pharm. Pharmacol. 1995; 47: 103-107.

Katz, U. and Shoenfeld, Y. "Review: intravenous immunoglobulin therapy and thromboembolic complications". Lupus, 2005; 14(10): 802-808.

(Continued)

*Primary Examiner* — Daniel E Kolker
*Assistant Examiner* — James Rogers
(74) *Attorney, Agent, or Firm* — RatnerPrestia

(57) ABSTRACT

A process for obtaining an IgG composition involves heat treatment. This process obtains an IgG composition from an IgG solution partly purified from human plasma, in which by applying intermediate heat treatment and without using reagents to precipitate high molecular weight aggregates/polymers and/or proteins virtually total elimination of the IgG polymers generated during the process is achieved. Furthermore this process offers high productivity, lower production costs and is easy to implement in comparison with the processes of the know art. In addition to this, by using this process stability is imparted to the final product in liquid.

28 Claims, No Drawings

(56) References Cited

OTHER PUBLICATIONS

Kistler, P. and Nitschmann, Hs. "Large Scale Production of Human Plasma Fractions". Vox Sang. 1962; 7: 414-424.

Koski, C. "Immunoglobulin use in management of inflammatory neuropathy". Pharmaceutical Policy and Law 2009; 11(4): 307-315.

Oncley, J.L. et al. "The separation of the antibodies, isoagglutinins, prothrombin, plasminogen and beta-1 lipoprotein into subfractions of human plasma". J. Am. Soc. 1949; 71: 541-550.

Radosevich, M. and Burnouf, T. "Intravenous immunoglobulin G: Trends in production methods, quality control and quality assurance". Vox Sang., 2009; 1-17.

Shukla, A. et al. "Strategies to address aggregation during protein A chromatography". Bioprocess International, May 2005.

Szenczi, A. et al. "The effect of solvent environment on formation and stability of human polyclonal in solution". Biologicals, 2006; 34(1): 5-14.

Teschner, W. et al. "A new liquid, intravenous immunoglobulin product (10% IGIV) highly purified by a state-of-the-art process". Vox Sang. 2007; 92(1): 42-55.

Uemura Y. et al. "Inactivation and elimination of viruses during the fractionation of an intravenous immunoglobulin preparation". Vox Sang. 1989; 56: 155-161.

Uemura, Y. "Dissociation of aggregated IgG and denaturation of monomeric IgG by acid treatment". Tohoku J. Exp. Med., 1983; 141: 337-349.

Vermeer, A. et al. "Thermal stability of immunoglobulin: Unfolding and aggregation of a multi-domain protein". Biophys. J. 2000; 78: 394-404.

International Search Report for corresponding application ES 201230413 dated May 16, 2012.

Aghaie, A., et al. "Preparation, purification and virus inactivation of Intravenous immunoglobulin from human plasma. Human Antiodies," 2010; IOS Press nld. vol. 19, No. 1, Paginas: 1-6; Isbn ISSN 1093-2607 (impreso). Doi: 10.3233/HAB-2010-0212.

Buchacher, A. et al., "Purification of intravenous immunoglobulin G from Human plasma-aspects of yield and virus safety." Biotechnology Journal Germany, (2006), vol. 1, No. 2, Paginas: 148-163; Isbn: ISSN 1860-6768 (impreso).

Carlsson, M. et al. "Purification of in vitro produced mouse monoclonal antibodies. A two-step procedure utilizing cation exchange chromatography and gel filtration." Journal of immunological Methods, (1985), vol. 79, No. 1, Paginas: 89-98; Isbn: ISSN 0022-1759; doi: 10.1016/0022-1759(85)90395-3.

* cited by examiner

PROCESS FOR OBTAINING AN IGG COMPOSITION THROUGH HEAT TREATMENT

CROSS REFERENCE TO RELATED APPLICATIONS

This application claims priority to Spanish Patent Application No. 2101230413, filed Mar. 20, 2012, the contents of which are incorporated herein by reference.

FIELD OF THE INVENTION

This invention relates to a new process for obtaining an IgG composition from a partly purified IgG solution from human plasma, in which by applying intermediate heat treatment step and without using reagents to precipitate high molecular weight aggregates/polymers and/or proteins almost total elimination of the IgG polymers generated during the process is achieved. In addition to this, the process offers high productivity, lower production costs and easier implementation in comparison with the processes in the prior art. Also stability for the final product in liquid is imparted through using this process.

Immunoglobulin G (IgG) is the isotype of the most abundant immunoglobulin in human serum (8-16 mg/ml), comprising approximately 80% of all immunoglobulins. IgG is indicated for the treatment of various diseases such as primary immunodeficiency, in particular congenital agammaglobulinaemia and hypogammaglobulinaemia, idiopathic thrombocytopenic purpura, as an adjuvant in the treatment of Kawasaki's Disease and in the transplant of bone marrow, hypogammaglobulinaemia associated with chronic lyphocyte leukaemia as part of the treatment of HIV infection in paediatric patients, among others.

BACKGROUND OF THE INVENTION

At the present time there is high demand for immunoglobulin G (IgG) which is polyvalent with a wide spectrum of human antibodies and has total functionality) neutralising capacity, opsonisation, average life conserved), with intact molecules (integrity of the crystallisable Fc fragment) and a normal distribution of IgG subclasses identical or equivalent to natural plasma, especially for the minority subclasses (IgG3 and IgG4).

The routes for the therapeutic administration of IgG may be intravenous, subcutaneous and intramuscular, and in addition to this it may be administered by other less conventional routes such as the oral, inhaled or topical routes.

Nevertheless intravenous administration offers the most useful therapeutic indications, whether for the treatment of primary immunodeficiencies or for variable common immunodeficiency (deficit of IgG and IgA subclasses) (Espanol, T. "Primary immunodeficiencies". Pharmaceutical Policy and Law 2009; 11(4); 277-283), which is incorporated herein by reference, secondary or acquired immunodeficiencies (for example infection by viruses such as cytomegalovirus, herpes zoster, human immunodeficiency) and diseases of an autoimmune origin *thrombocytopenic purpura, Kawasaki's Syndrome, for example) (Koski, C. "Immunoglobulin use in management of inflammatory neuropathy". Pharmaceutical Policy and Law 2009; 11(4): 307-315), which is incorporated herein by reference.

Ideally IgG for intravenous use (IGIV) should be formulated with a high concentration in liquid and preferably should be capable of being stored up to approximately 30° C. in order to facilitate conservation of the product and immediate infusion.

It has been described that in order to reduce possible IgG intolerance reactions it is necessary that immunoglobulin A (IgA) and immunoglobulin M (IgM), as well as blood group agglutinins, should be absent, or in an undetectable quantity. It is also essential that the product should be virtually free of any enzyme activity, both through the presence of plasmin or plasminogen, or prekallikrein, or its activators, kinins or kininogen, or coagulation factors such as factor XI/factor XIa, among others.

On the other hand the human origin of the starting plasma for obtaining polyvalent IgG makes it necessary to reduce the risk of infection through the transmission of viruses or pathogens to a minimum. As described by Fernandes et al. (ES 500121) and Hirao, Y. et al. (EP 196761 and EP 253313), which are incorporated herein by reference, heat treatment of IgG in solution (liquid), or pasteurisation, can be performed effectively in the presence of protectors against denaturing of the IgG (e.g., saccharose, sorbitol, amino acids). For this purpose the solution is raised to a temperature of approximately 60° C. for at least some 10 hours, activating or attenuating the most dangerous pathogens. These pathogens may have a lipid coat such as human immunodeficiency virus (HIV), hepatitis C virus (HCV) and hepatitis B virus (HBV), or be naked, such as poliovirus, hepatitis A virus (HAV) and parvovirus, among others (Uemura Y. et al. "Inactivation and elimination of viruses during the fractionation of an intravenous immunoglobulin preparation". Vox Sang. 1989; 56: 155-161), which is incorporated herein by reference.

Nevertheless, pasteurisation, even in the presence of stabilisers and under the best process conditions, inevitably results in the formation of irreversible high molecular weight protein aggregates such as IgG polymers and/or polymers of other accompanying proteins, in greater or lesser proportion depending upon the purity of the starting IgG (Hirao, Y. et al., above; and Ristol, P. et al. EP 1225180 and ES 2091161), which are incorporated herein by reference.

During the decade 1960-1970 the presence of irreversible high molecular weight aggregates known as IgG polymers was associated with the consumption of complement for activation of the same (anticomplement activity, ACA) during the intravenous administration of IgG, and this phenomenon was linked to severe intolerance or anaphylaxis reactions observed (Barandum, S. et al. Vox Sang. 7: 157-174, 1962), which is incorporated herein by reference. Because of this health authorities regulated the maximum content of polymers in IGIV, or molecular forms higher than dimers, to a limit of 3% (Eur.Ph. Monograph 6.3; and CMP Core SPC for normal immunoglobulin for intravenous administration: CPMP/BPMG/859/95 rev.2), which is incorporated herein by reference. This consideration is especially important for a liquid formulation because the 3% limit must also be maintained up to the expiry date for the product. A virtually total absence of these IgG polymers must therefore be achieved, both after pasteurisation and in the final product obtained, to ensure that the product will not deteriorate over the long term and ensure the maximum possible storage temperature.

At the present time most of the liquid IgG available on the market and formulated with amino acids must maintain an acid pH to avoid aggregation (Uemura, Y. "Dissociation of aggregated IgG and denaturation of monomeric IgG by acid treatment". Tohoku J. Exp. Med., 1983; 141: 337-349), which is incorporated herein by reference, preferably between a pH of 4.0-5.0 (Tenold, R. et al. U.S. Pat. No. 4,396,608, which is incorporated herein by reference) and at a temperature of 2-8°

C. if they are stabilised with 0.2 M or 0.25 M glycine, such as those known by the trade names of Gamunex® (Grifols S A, Spain), Kiovig® or Gammagard® Liquid (both from Baxter, United States), or up to 25° C. if stabilised with 0.25 M proline, such as Privigen® (CSL Behring, Germany), in order to minimise molecular aggregation during storage (Jolles, S. et al. "Clinical uses of intravenous immunoglobulin". Clin. Exp. Immunol. 2005 October; 142(1): 1-11; Hooper, J. A. "Intravenous immunoglobulins: evolution of commercial IVIG preparations". Immunol Allergy Clin. North Am. 2008; 28(4): 765-778), which are incorporated herein by reference.

It has been demonstrated that an excessively acid pH over a long period of exposure favours the fragmentation of IgG, for example at a pH of 4.5 or below and at a relatively high temperature, for example at 30° C. (Vermeer, A. et al. "Thermal stability of immunoglobulin: Unfolding and aggregation of a multi-domain protein". Biophys. J. 2000; 78: 394-404; Shukla, A. et al. "Strategies to address aggregation during protein A chromatography". Bioprocess International, May 2005, which are incorporated herein by reference). Thus for example it has been reported in the literature that 10% IGIV compositions formulated with L-proline at a pH of 4.8±0.2 are sufficiently stable with regard to molecular aggregation, but a tendency to fragmentation with exposure time is observed. Thus at a temperature of 25° C. fragments amount on average to 3.9% after 36 months (Cramer, M. et al. "Stability over 36 months of a new liquid 10% polyclonal immunoglobulin product (IgPro10, Privigen®) stabilised with L-proline", Vox Sang. 2009. DOI: 10.1111/j.1423-0410.2008.01143.x, which is incorporated herein by reference).

It has been described that the formulation of IgG with polyols or poly-alcohols, for example with maltose and sorbitol, prevents aggregation (Katakam, M. et al.: Aggregation of proteins and its prevention by carbohydrate excipients: Albumins and globulin. J. Pharm. Pharmacol. 1995; 47: 103-107), which is incorporated herein by reference, and because of this property IgG solutions that are stable up to 25° C. (with 10% maltose, trade name Octagam®) and up to 30° (with 5% sorbitol, trade name Flebogamma® DIF) have been formulated in a slightly acid pH range between 5.0 and 6.0 (Hirao, Y. et al., patent EP-278422), which is incorporated herein by reference.

However the presence of some sugars or derivatives in IgG formulations has been questioned in recent years (Szenczi, A. et al.: The effect of solvent environment on formation and stability of human polyclonal in solution. Biologicals, 2006; 34(1): 5-14), which is incorporated herein by reference, as some cases of serious kidney failure have been associated with the infusion of IgG preparations containing saccharose. Other disadvantages that may be presented by some immunoglobulin compositions with particular sugars (saccharose) and some high concentrations of polyols (10% maltose) is the relative capacity to increase blood viscosity when infusing the solutions, this being linked to some very serious cases of intravascular thrombosis and acute myocardial infarction where there is previous disease or the patient is at risk (Radosevich, M. and Burnouf, T. "Intravenous immunoglobulin G: Trends in production methods, quality control and quality assurance." Vox Sang., 2009; 1-17; Katz, U. and Shoenfeld, Y.; Review: intravenous immunoglobulin therapy and thromboembolic complications. Lupus, 2005; 14(10): 802-808, which are incorporated herein by reference).

It has also been detected that some commercial IGIV products contain active procoagulating enzymes, remnants from their process of purification, which have a marked thromboembolic effect (TEE), and an association between TEE and the presence of factors XI/XIa and/or other procoagulant factors (e.g. kallikrein or the like) has been proved. Elimination of thromboembolic capacity is an imperative which must be fulfilled for IGIV infusions, with maximum guarantees of tolerance and safety.

BRIEF DESCRIPTION OF THE INVENTION

Without being associated with any particular theory the present inventors believe that the main differences between currently marketed IGIV can be attributed not only to the formulation (amino acids, sugars and polyols, and pH) but also the process for obtaining the IgG, which will affect the final conservation conditions for the product in liquid (temperature-time), for example to prevent aggregation and fragmentation during storage, among other characteristics. This dependency between the stability of liquid IgG formulations and their process of purification has been observed by other authors (Cramer, M. et al. above).

This invention therefore provides a process for obtaining an IgG preparation that overcomes the problems in the state of the art previously mentioned. The process according to this invention starts with a material containing IgG purified by conventional method, which is additionally purified by heat treatment, also known as pasteurisation, under specific conditions of stabilising agents, protein concentration, conductivity, pH and residual reagent concentration from previous precipitation steps that make it possible to reduce protein and proteolytic enzyme impurities. This reduction in the impurities and enzymes occurs during this treatment and/or during a step subsequent to selective adsorption of the aggregated proteins, but in any event these two steps are exclusively used as a final purification without introducing separation techniques using precipitation.

The prior art includes the industrial scale use of a combination of aggregate/polymer precipitation and chromatographic separations, such as described for example by Coval, L. (U.S. Pat. Nos. 4,093,606 and 4,165,370) and Uemura, Y. et al. (Patents ES-506679 and EP-246579), which are incorporated herein by reference, which described precipitation processes using polyethylene glycol (PEG), a poorly selective method which causes high recovery losses of IgG monomer/dimer (coprecipitation), which vary greatly according to the process used. For example, if heat treatment is carried out in an IgG solution that has not been sufficiently purified IgG recovery (monomer/dimer) will normally be between 70 and 80% (Usemura, Y. et al. above). In the case of purified IgG solutions better recovery results can be obtained, with 80-90%, but for this it is necessary to use complex separation techniques such as tangential flow microfiltration (TFF), as described in the prior art (Ristol, P. et al., above). However the TFF process is associated with a high consumption of precipitation reagents (PEG), stabiliser (sorbitol) and water for injection, and a number of cleaning-sanitisation operations which have to be considered when equipment is necessarily reused. It is furthermore associated with a long process time, may be difficult to handle, the associated costs for consumables and/or energy are high and IgG monomer/dimer recovery is always less than 90%.

DETAILED DESCRIPTION OF THE INVENTION

The present authors have developed a process through which the use of reagents to precipitate high molecular weight aggregates/polymers and/or proteins as described in the prior art has been dispensed with, and surprisingly have achieved virtually total elimination of the polymers generated, with high productivity, lower production costs and easy implementation in comparison with the processes in the prior art. Furthermore, through the use of this process, stability has been achieved for the final product in liquid, preferably formulated in the presence of amino acids or polyalcohols, and it may be kept in liquid for at least 1 year at a temperature of between 2 and 30° C. and a pH of 4.6 or above and up to 5.8.

This invention therefore relates to a process for obtaining an IgG composition from a partly purified IgG solution from human plasma which comprises the steps of:
a) diafiltering the partly purified IgG solution;
b) stabilising the solution obtained in step a);
c) heat treating the solution obtained in step b);
d) selectively adsorbing the high molecular weight aggregates and/or polymers from the heat treated solution in step c) through cation chromatography; and
e) diafiltering and formulating the solution obtained in step d).

Through the use of this process a significant reduction in the high molecular weight aggregates/polymer content, that is to say those higher than the dimer of IgG and other unstable proteins, is achieved, giving rise to a solution which essentially contains IgG monomers/dimers that can be formulated in a slightly acid medium, and can be kept in a liquid at ambient temperature without noticeable signs of instability, complying with the specifications established for its preferably intravenous, or subcutaneous or intramuscular use.

Preferably the process according to this invention is performed starting from a purified IgG solution of human plasma having an IgG content more than 95% with respect to total proteins and more preferably more than 97%, as determined by electrophoresis in cellulose acetate, starch black tinction, and quantified densitometrically, in accordance with the method described in the European Pharmacopoeia.

As starting materials this patent considers the use of IgG-rich fractions (separated from the fractioning of human plasma to obtain albumin by conventional methods known in the art), followed by their appropriate purification to start the process according to the invention.

Hitherto cold fractionation of plasma with ethanol, based on method 6 by Cohn (Cohn, E. J. et al. Separation into Fractions of the Protein and Lipoprotein Components. J. Am. Chem. Soc. 1946; 68: 459-475, which is incorporated herein by reference) to separate out an IgG-rich fraction mostly continues in use, and on an industrial scale. This fraction (Fr-II+III) or equivalent (Fr-I+II+III), which contains most (≥90%) of the IgG and plasma, of variable purity (normally between 35 and 65% of IgG in relation to the other proteins), has to be purified more extensively through precipitations with ethanol know as Cohn-Oncley method 9 (Oncley, J. L. et al.: The separation of the antibodies, isoagglutinins, prothrombin, plasminogen and beta-1 lipoprotein into subfractions of human plasma. J. Am. Soc. 1949; 71: 541-550, which is incorporated herein by reference) until a concentrated immunoglobulin fraction (Fr-II, or supernatant of concentrated Fr-III) is obtained. Another viable alternative is to use the Kistler-Nistchmann method (Kistler, P. and Nitschmann, Hs. Large Scale Production of Human Plasma Fractions, Vox Sang. 1962; 7: 414-424, which is incorporated herein by reference) as far as precipitate A (or equivalent precipitate A+I), and then purify this to obtain the GG precipitate, or to the concentrated supernatant (ultrafiltrate) of precipitate B.

Using both precipitation procedures with ethanol it is possible to obtain an IgG solution (from Fr-III supernatant, Fr-I+III, Fr-II, precipitated GG or supernatant of precipitate B) which complies with the minimum purity characteristics of ≥95% of IgG (through electrophoresis on cellulose acetate) and preferably ≥97% of IgG, which is required so that it can be used as a starting material in the process according to the invention. This converts IgG which is acceptable for the intramuscular of subcutaneous route into a preparation which is tolerable for the intravenous route.

In any event, at the present time other preferred combinations are used to increase the purity of the starting material (e.g. Fr-II+III or precipitate A), for example, by precipitation of the majority contaminants and/or their adsorption on anionic resins and/or inorganic adsorbents (polyethylene glycol, octanoic acid, ion exchange chromatography, bentonite, perlite). Documents Ristol, P. et al. EP-1225180; Lebing, W. et al. EP-0893450, which is incorporated herein by reference; Teschner, W. et al.: A new liquid, intravenous immunoglobulin product (10% IGIV) highly purified by a state-of-the-art process. Vox sang. 2007; 92(1): 42-55, which is incorporated herein by reference, relate to valid processes for purification through precipitation with ethanol, PEG or octanoic acid, combined with ion exchange chromatography to increase the purity of an intermediate IgG fraction (for example Fr-II+III) up to ≥95% of IgG, and preferably ≥97% of IgG before proceeding to the purification treatment in the patent.

The diafiltration in step a of the process according to this invention is carried out with the aim that the concentration of undesirable components deriving from a standard IgG purification process be reduced below concentration values which can affect the process according to this invention. For example, one undesired component is ethanol, and through this diafiltration step (a) this should be reduced to a concentration of less than 0.5% (weight/volume), preferably less than 0.1%. If other non-denatured precipitation reagents such as PEG, octanoic acids, compatible non-ionic detergents or any mixture thereof are present, the concentration of these must also be reduced to less than 2% (weight/volume) and in any event till they do not give rise to more than 3% of polymer after step c).

Furthermore, in this diafiltration step the starting IgG solution may be adjusted to an ionic strength whose conductivity is less than 1 mS/cm, and the pH is adjusted to between 4.0 and 5.5, preferably in both cases. Diafiltration may be carried out with water for injection or preferably with a buffer solution of low ionic strength such as a solution of ≤5 nM acetic acid or sodium acetate solution adjusted to pH 4.0-5.0 with alkali or dilute acid.

Dialiltration step (a) is preferably carried aut in tangential flow mode across ultrafiltration membranes, of for example polyethersuifone or equivalents, using a molecular cut-off between 10 kDa and 100 kDa. Beneficially in the process according to this invention, diafiltration step (a) also serves to concentrate the proteins up to a concentration of not more than 5% (weight/volume), preferably between 2% and 4% (weight/volume).

Once the solution step (a) has been obtained, this is stabilised, for example through the addition of sorbitol as a stabilising agent up to a maximum concentration of 50% (weight/weight), preferably between 30% and 35% by weight. In addition to this the pH is adjusted to between 4.2 and 6.0, preferably between pH 4.6 and 5.2 through the addition of acid (for example hydrochloric acid or acetic acid) or alkali (for example sodium hydroxide) in a manner which is known in the art.

The heat treatment or heating of the solution in step (c) of the process according to this invention is a special procedure also know as pasteurisation, and is carried out at a temperature of between 55° C. and 63° C. for a time of between 1 and 24 hours. Although the solution can be heat treated at any temperature and for any time within the ranges mentioned above, heat treatment is preferably carried out at 60±1° C. for 10-11 hours. In any event not more than 3% of high molecular weight polymers/aggregates, and preferably between 1% and 2%, should be generated. Likewise proteolytic activity due to the possible presence of procoagulating factors, for example factor XI/XIa or other proteases, measured chromogenically for different substrates (S-2303, S-2288 and S2238) as described in the art (see Example 3) is reduced at least 5 times in comparison with its initial contents.

Subsequently the solution is cooled, preferably between 18° C.-30° C. and diluted, preferably with at least 33% (by weight) of water for injection, or more preferably with buffer solution containing a compatible salt (for example sodium acetate, phosphate, citrate or the like) at a concentration of preferably ≤20 mM. Once diluted the solution contains a sorbitol concentration ≥5% by weight, and a protein concentration ≥5 mg/ml. A totally ionisable compatible salt, preferably sodium chloride, as solid or in concentrated solution, for example 3 M (mol/liter) is added to this solution until a sodium chloride solution of between 0.20 M (mol/liter) and 0.50 M (mol/liter), preferably between 0.25 M (mol/liter) and 0.40 M (mol/liter) is obtained. If necessary the pH can be adjusted again to between 4.2 and 5.5, and preferably between 4.5 and 5.0, by the addition of preferably dilute hydrochloric or acetic acid and/or sodium hydroxide.

The solution conditioned in the manner described above, that is to say after dilution, adjustment of the salt concentration and pH, which contains a maximum of 5% of dimers, is injected into a chromatography column containing strong cation exchange perfusion resins having at least one of the cationic sulfonic groups (sulfonyl, sulfonic or sulfopropyl: S, HS, SP groups) joined covalently to a synthetic insoluble and virtually incompressible perfusion matrix comprising rigid particles of polymethacrylate or polystyrene, and preferably comprising a matrix or support of particles of polystyrene, polyvinyl benzene of between 20-100 μm. The resin may be packed in a cylindrical axial flow column of appropriate diameter for packing, occupying preferably between some 5-20 cm height of resin, or packed in a radial flow column with a path of between preferably 10-15 cm. In both cases at least 1 liter and preferably between 1 and 10 liters of that resin are used for each kg of (dry) IgG which has to be purified, which is equivalent to a loading of between 100 and 1000 mg of IgG/ml of gel. Preferably the quantity of resin packed in the column used is between 2 and 5 liters per kg of IgG (equivalent to a loading of 200-500 mg IgG/ml of gel). Before injecting the product the column is equilibrated with a buffer solution containing preferably sodium acetate between approximately 5 and 50 mM (millimolar) and more preferably 10 mM (millimol/liter), and a sodium chloride concentration (if that is the chosen salt added to the product) which is approximately equal or equivalent to that of the product. The preferred injection flow is not more than 50 column volumes/hour, and more preferably between 5-30 column volumes/hour, the preferred temperature being 18° C.-30° C. IgG monomers/dimers pass freely through the column, more than 90% of the total monomers plus applied dimers being recovered in the effluent (adsorption is <10% of monomers/dimers), and preferably a recovery of ≥93% is achieved, this effluent being recovered in a pool up to an appropriate volume.

Simultaneously the aggregates/polymers are captured by the resins to an amount of ≥85% of their initial content, which is equivalent to a more than 5-fold reduction, preferably a reduction ≥95% (≥20 times) of the initial content in the material originating from the heat treatment, with ≤0.3% of polymers and preferably ≤0.1% or ≤0.06% being found (unadsorbed) in the column effluent pool. Likewise by suitably increasing the loading in the column and applying post-washing, for example with at least two column volumes of a solution equal or equivalent to that used to equilibrate the column, monomer/dimer recovery can even be increased most preferably up to ≥95%. Thus recoveries of ≥95% can be achieved, reinjecting the regeneration fraction into the same column, suitably diluted and adjusted to the conditions used in the initial loading or of less ionic strength. Injection by decreasing gradient, as already indicated, also encourages the recovery of IgG monomers/dimers and a person skilled in the art could easily achieve a product recovery ≥95% in this way or using a similar process. To do this loading is started with a maximum salt concentration according to the pH in order to minimise super-adsorption phenomena in the first volumes applied, progressively increasing the capacity of the resin as the ionic strength decreases, until the loading volume is completed. For example, a decreasing gradient of up to 15% between the salt concentration of the product selected at the start of loading in comparison with that at the end thereof may preferable be used.

Optionally the process according to this invention may comprise one or more of viral inactivation/elimination treatments complementing heat treatment of the solution. Among the viral inactivation treatments which may be used in the process according to the invention are incubation at acid pH (for example pH 3.8-4.2 at 37±2° C. for between 4-24 hours in the presence or absence of pepsin, or non-ionic detergents such as Pluronic, Triton, Tween and the like); treatment with an alkyl phosphate organic solvent (0.3% tri-n-butyl phosphate of TNBP); detergents (1% Triton X-100 or Triton X-45) (Neurath et al. U.S. Pat. No. 4,540,573 (U.S. Ser. No. 514, 375), which is incorporated herein by reference), preferably by adjusting the IgG solution to pH 4.2-6.0 and the temperature to 4-30° C., incubating for 1-12 hours, and more preferably some 6 hours at 25±2° C.; and viral retention membrane nanofiltration (regenerated cellulose, polyether sulfone, polyvinylidene fluoride), through either tangential or terminal flow, in the form of a cassette or sandwich (flat surface), cartridge (folded, sheet, disks) or hollow fibre, preferably through a pore size ≥50 nm, approximately between 10-50 nm and preferably between some 15-35 nm and preferably 20±2 nm pore size, with terminal nanofiltration. These inactivation/elimination steps may be carried out before or after the heat treatment step, except when using nanofiltration, where it is preferably that it should be used before the heat treatment.

Once step (d) of the process according to this invention has been completed the solution obtained is diafiltered with water for injection or preferably with a buffer solution of low ionic strength which may for example contain ≤5 mM of acetic acid at a pH of 4.0-5.5, and optionally stabilisers or excipients for the final formulation. The final diafiltration is carried out by tangential flow through ultrafiltration membranes of polyethersulfone or equivalent, using a molecular cut-off preferably between 10 kDa and 100 kDa, and more preferably between 30 kDa and 50 kDa. After an appropriate number of diafiltration volumes to reduce the salt concentration, preferably to a conductivity of ≤2 mS/cm, protein is preferably concentrated in nominal concentrations of 5%, 10%, 16% or 20% or any other intermediate concentration between approximately 5% and 22% (w/v). The solution is preferably stabilised through the addition of a polyalcohol (polyol) or amino acids. In any event the osmolality of the resulting solution will be ≥240 mOsm/kg, and approximately isotonic. Preferably the pH is adjusted to 5.2±0.6 and a check is made to ensure that it lies between 4.6 and 5.8, readjusting with dilute acid or alkali if necessary.

The adjusted solution is sterilely filtered through an absolute membrane of 0.2 μm pore size in a manner known in the art. The liquid solution obtained is aseptically metered into appropriate containers and subjected to incubation (quarantine) of not less than 14 days at 25±5° C., preferably in order to observe any sign of instability or contamination in each individual metered unit. The contained product is stored under the same conditions as for quarantine (ambient temperature 25±5° C.) or in a cold chamber (5±3° C.). The product obtained by the process according to this invention remains stable (essentially unalterable) for at least 1 year at a temperature of between 2-30° C. without showing any signs revealing degradation in either its physical characteristics (appearance, colour, turbidity, sediments, particles or fibres) or its specification analytical parameters according for example to the European Pharmacopoeia (high molecular weight aggregates, fragments, anticomplement activity of ACA, prekallikrein activator or PKA, subclasses of IgG, etc.).

This invention is described in greater detail below with reference to examples. These examples are however not intended to restrict the technical scope of this invention.

EXAMPLES

Example 1

Starting with a mixture of frozen human plasma suitable for fractionation, this was cryoprecipitated at a temperature between 0 and 4° C. The cryoprecipitate was separated by continuous flow centrifuging (Westfalia centrifuge) at the same cryoprecipitation temperature. The supernatant was processed in accordance with Cohn fractionation method 6 (Cohn et al., above) using cold ethanol until Fr-II+III was obtained. The paste obtained or precipitated (Fr-II+III) was separated by press filtration and frozen at ≤20° C. Subsequently Fr-II+III was processed by Cohn-Oncley fractionation method 9 (Oncley, J. et al., above) until Fr-II was obtained. The Fr-II obtained was stored at ≤20° C.

The Fr-II was suspended in an isotonic solution of glycine and sodium chloride and adjusted to approximately neutral pH. The solution was treated with inorganic adsorbents, separated by centrifuging (RINA centrifuge) and then clarified on a filter of pore depth ≤0.5 μm.

The filtrate was adjusted to a pH between 5.5 and 6.0 using 0.5 M HCl and ultrafiltered through polysulfone membranes having a nominal molecular cut-off 10 kDa. The volume was first reduced and then diafiltration was started at constant volume with water for injection at 2-8° C. On completion of this the ultrafiltration equipment was post-washed and the solution was adjusted to an optical density (at 280 nm) of 60±5 AU of protein. Solid sorbitol was added in an amount of 0.5 kg for each kg of the solution present and after dissolving the pH of the solution was adjusted to 5.5±0.5 using 0.5 M HCl.

Heat treatment of the solution was then carried out in a thermostatic container recirculating the heating fluid through the jacket in such a way that the product was raised to between 60 and 61° C. and held there for 10-11 hours. The solution was then cooled to 2-8° C.

The results obtained for the average of 3 separate lots are shown in Table 1.

TABLE 1

| STEP IN THE PROCESS | TOTAL PROTEIN (%) (O.D. 280 nm) | PURITY (% IgG electrophor.) | POLY-MERS (%) | ETHA-NOL (% v/v) | CONDUCT. (mS/cm) |
|---|---|---|---|---|---|
| Suspension Fr-II | 6 | ≥97 | ~0.2 | 3.3 (3.2-3.4) | ~10 |
| Ultra-filtered solution | 4 | ≥97 | 0.21 (0.19-0.23) | ≤0.1 | ≤0.5 |
| Heated solution (10 h at 60-61° C.) | 3 | ≥97 | 1.58 (1.30-1.86) | ≥0.1 | ≤0.5 |

The above results show the effect of the prior purification of Fr-II+III (FrII suspension ≥97% by electrophoresis) and reducing denaturing agents (ethanol) on aggregation during heat treatment, with only 1.58% of polymers, making subsequent adsorption by synthetic cationic resins possible.

Example 2

Starting with a pool of human plasma, the process was the same as described for Example 1 until Fr-II+III was obtained (test a) and continued to Fr-II (test b). In order to establish the effect of purification, as well as the presence of denaturing agents on polymerisation during heat treatment, the procedure was as follows:

a) The Fr-II+III was suspended in water for injection at 2-8° C. in a proportion of 1:3.5 by weight, and after a homogeneous suspension had been obtained the pH was raised to 5.25±0.25 with 0.5 M HCl, Subsequently this was centrifuged in a decanter (centrifugal force between 200 g-1000 g) yielding a clarified suspension.

b) Fr-II was processed as in Example 1 until a solution clarified by a deep filter was obtained.

Each of the above solutions was stabilised through the addition of solid sorbitol in an amount of 0.5 kg per kg of starting supernatant. After the sorbitol had been dissolved the pH was adjusted to 5.5±0.5 if necessary. Each solution was heated to 60-61° C. for 10-11 hours. It was then cooled to 2-8° C.

The results obtained from the pasteurised product in tests a) and b), in comparison with Example 1, are shown in Table 2.

TABLE 2

| TEST OF PROCESS | TOTAL PROTEIN (%) (O.D. 280 nm) | IgG PURITY (%) | POLY-MERS (%) | ETHA-NOL (% v/v) | CONDUC-TIVITY (mS/cm) |
|---|---|---|---|---|---|
| Test a) | 4 | 75 | 15 | 2.5 | 2 |
| Test b) | 4 | ≥97 | 5.03 | 2.5 | ≤0.5 |
| Process Example 1 | 4 | ≥97 | 1.58 | ≤0.1 | ≤0.5 |

The results of tests a) and b) demonstrate the effect of the purity of the starting IgG and the need to achieve values ≥97%. On the other hand, comparing test b) with the process in Example 1 the effect of the residual ethanol originating from ethanol fractionation and the need to eliminate it is obvious. It is therefore deduced that only the conditions in Example 1 would be acceptable for the process according to the invention.

Example 3

The plasma was fractionated in the same way as in Example 1 as far as Fr-II+III, and this material was purified with PEG or anionic exchange resins until a sufficiently pure product was obtained.

The same process conditions as described in the description of patent EP 1225180 were applied for this initial purification of Fr-II+III. In more detail, in this example Fr-II+III was suspended in aqueous solution containing sorbitol, disodium phosphate and acetic acid until all the IgG was effectively dissolved. The main accompanying proteins were precipitated out by the addition of up to 4% of PEG. After this inorganic adsorbents and filtration coadjuvant were added. Before separating out the precipitate by press filtration (cellulose press filters) the pH was readjusted to 5.0±0.5. The paste was separated and the filtrate pool collected. Injection was into a chromatography column containing DEAE-Sepharose® (Amersham Biosciences, Sweden) type anion exchange resins following adjustment of pH and clarifying gradient filtration up to ≤0.5 μm just before entry into the column. All the effluent obtained during loading the product containing purified IgG was collected.

The above effluent was adjusted to pH 4.4±0.2 with 0.5 M HCl and ultrafiltered through polysulfone membranes having a nominal molecular cut-off 100 kDa. Initially the volume was reduced some 4 times to yield a concentration of 2% of protein and then diaftitration at constant volume with 4 volumes of water for injection with 4 mM acetic acid (millimol/liter) and 5% sorbitol adjusted to pH 4.2±0.2 with 0.5 M NaOH was initiated at 2-8° C. On completion of this the ultrafiltration equipment was post-washed yielding a solution of an optical density (at 280 nm) of 55±5 AU of protein. Subsequently 0.5 M HCl was added up to a pH of 4.0±0.1 followed by incubation at 36±1° C. for 4 hours.

Solid sorbitol was then added in a quantity of 0.43 kg for every kg of the present solution (33% weight/weight), and after it had dissolved the pH of the solution was adjusted to 4.9±0.1 with 0.5 M NaOH.

Heat treatment was performed in a thermostatted vessel recirculating heating fluid through the jacket so that the product was raised to 60-61° C. and held there for 10-11 hours. Then the solution was cooled to 2-8° C. The analytical composition results for monitoring the process are shown in Table 3.

TABLE 3

| STEP IN THE PROCESS | TOTAL PROTEIN (%) | IgG PURITY (%) | POLYMERS (%) | ETHANOL (%v/v) | PEG (%) | CONDUCTIVITY (mS/cm) |
|---|---|---|---|---|---|---|
| Fr-II + III suspension | n.d. | 70 | 12 | 1 | 0 | 1.5 |
| Purified column effluent solution | n.d. | ≥98 | ≤0.06 | 0.8 | 4 | 1.2 |
| Ultrafiltered solution | 4.0 | ≥98 | ≤0.06 | ≤0.1 | 0.8 | ≤0.5 |
| Heated solution (10 h at 60° C.) | 2.8 | 98 | 1.5 | ≤0.1 | 0.5 | ≤0.5 | n.d.: not determined

The results in Table 3 indicate that a residual PEG content of 0.8% does not affect the degree of polymerisation during heat treatment (1.5% of polymers). Likewise this polymerisation is not affected by the method of purification previously used, whether using ethanol alone or ethanol+PEG+anion chromatography (see Examples 1 and 2), provided that the purity achieved is of the same order (≥97% of IgG).

Likewise analytical determinations on different chromogenic substrates were performed on other lots on a preparative scale processed in the same way as described previously in this Example 3 in order to evaluate the steps having the ability to inactivate proteolytic enzymes, mainly procoagulants. Substrates S-2302, S-2288 and S-2238 (specific for coagulation factors for the prothrombin complex, thrombin, plasminogen/plasmin, FXI/FXIa, FXII PKA, etc.) were used on the basis of the technique described according to the state of the art, calculating the gradient of the kinetics of the chromogenic reaction in optical density (O.D.) absorption units per minute (min) in relation to the applied protein concentration (g/ml). The ratio (O.D./min)/(g/ml) in the steps before and after pasteurisation is shown in Table 4.

TABLE 4

| STEP IN THE PROCESS | PROTEOLYTIC ACTIVITY (O.D./min)/(g/ml) | | |
|---|---|---|---|
| | S-2302 | S-2208 | S-2238 |
| Purified column effluent solution | 1.69 | 2.03 | 0.23 |
| Ultrafiltered solution | 0.87 | 1.1 | 0.14 |
| Heated solution (10 h at 60° C.) | 0.12 | 0.14 | 0.017 |

It will be seen from the results in Table 4 that under the specific conditions of the pasteurisation process proteolytic activity (mainly procoagulant factors) can be reduced more than 5 times in comparison with initial content (ultrafiltered solution) according to values obtained with the three different chromogenic substrates used.

Example 4

Three different production lots processed in the same way as in Example 3 until a pasteurised solution for each was obtained were available. Each solution was diluted some 4 times with 10 mM (millimol/liter) sodium acetate solution at some 20-25° C. to achieve some 10 AU of optical density (at 280 nm), and some 8% by weight sorbitol concentration, adding the quantity of NaCl required to bring the product to a final concentration of 0.4 M (mol/liter). The solution was adjusted to pH 4.5 through the addition of dilute HCl (0.1 M-0.5 M).

The solution was injected into a strong polystyrene cation chromatoqraphy column (POROS HS® 50 μm. Applied Biosystems, United States), of some 8 ml in aolume (height 10 cm×0.8 cm² cross-section. The column was equilibrated with some 10 column volumes of a 10 mM buffer solution of sodium acetate solution at a pH and NaCl concentration equal to that of the product being loaded. The product was injected at a flow of some 20 column volumes/hour, with all the effluent from the column from the start of injection being collected. The sample of the effluent at a fixed volume of 16 column volumes corresponding to a loading of some 155 mg of IgG/ml of gel was obtained, the protein in being determined by O.D. (280 nm) and the polymer content by HPLC in order to calculate the % recovers of IgG (monomers/dimers) and the % reduction in polymers achieved. Table 5 shows the results obtained.

TABLE 5

| PROCESS | O.D. (280 nm) DILUTED SOL. (AU) | PROTEIN RECOVERY (%) | INITIAL POLYMERS (%) | FINAL POLYMERS (%) | REDUCTION IN POLYMERS (%) |
|---|---|---|---|---|---|
| Lot A | 10 | n.d. | 1.90 | 0.11 | 94 |
| Lot B | 10 | n.d. | 1.82 | 0.09 | 95 |
| Lot C | 10 | 96 | 2.51 | 0.15 | 94 | n.d.: not determined

Consistently with the previous results, a very significant and consistent reduction in polymers content, of between 94% and 95%, was obtained, and a final content of between 0.09 and 0.15 was obtained for an initial polymer content of between 1.8% and 2.5%. On the other hand IgG recovery (monomer/dimer) of 96%, together with a loading capacity exceeding 100 mg IgG/ml of gel and a process time of less than 2 hours (equilibrating and loading) should be noted.

Example 5

The process used was the same as in Example 4, but loading capacity at different injection volumes under the conditions established in Example 4 ware investigated. Samples of effluent for different applied volumes were taken, determining protein by O.D. (280 nm) and polymer content by HPLC to calculate the % recovery of IgG (monomers/dimeesj end the % reduction in polymers achieved for different loading values (mg of IgG/ml of gel). The results are shown in Table 6.

TABLE 6

| COLUMN VOL. (CV) APPLIED | INJECTED LOADING (MG IgG/ml gel) | POLYMERS (EFFLUENT) (%) | REDUCTION IN POLYMERS (%) | PROTEIN RECOVERY (IgG) (%) |
|---|---|---|---|---|
| Initial loading solution | 0 | 2.51 | 0 | 100 |
| 2 | 14 | ≤0.06 | ≥98 | 87 |
| 16 | 115 | 0.15 | 94 | 95 |
| 32 | 230 | 0.19 | 92 | 95 |
| 50 | 360 | 0.25 | 90 | 97 |

The results demonstrate very significantly that loading values of 360 mg of IgG/ml of gel can be achieved under normal flow conditions of up to 20 column volumes per hour with maximum IgG recovery, maintaining the ability to reduce polymers below the 0.3% limit up to 50 applied column volumes in a sustained way. The process time for the loading utilised did not exceed 3 hours.

Example 6

In order to know the operating range of NaCl concentration at an established pH of 4.5 and to optimise polymer elimination by maximising IgG recovery the procedure was as in Example 4, but different NaCl concentrations between 0.35 and 0.425 M were studied, sampling the column effluent at 2 CV, 25 CV and 50 CV to determine protein by O.D. (280 nm) and polymers by HPLC, to calculate the % recovery of protein and polymer reduction. The results obtained are shown in Table 7.

TABLE 7

| COLUMN VOLUME (CV) APPLIED | INJECTED LOADING (mg IgG/ml gel) | EFFLUENT POLYMER AT DIFFERENT NaCl CONCENTRATIONS (%) | | | |
|---|---|---|---|---|---|
| | | 0.425M | 0.40M | 0.375M (n = 2) | 0.35M |
| Initial loading solution | 0 | 1.88 | 2.12 | 2.13-2.14 | 1.99 |
| 2 | 14 | 0.10 | n.d. | ≤0.06 | ≤0.06 |
| 25 | 180 | 0.27 | 0.11 | ≤0.06 | ≤0.06 |
| 50 | 360 | 0.33 | 0.31 | ≤0.06 | ≤0.06 |
| Loading effluent pool at 50 CV | 360 | n.d. | n.d. | ≤0.06 | ≤0.06 | n.d.: not determined

Table 8 shows, the results of TgG recovery and polymer reduction in the effluent for the final mantraum applied loading value (50 CV).

TABLE 8

| NaCl CONCENTRATION (M) AT pH 4.5 | IgG RECOVERY (%) | REDUCTION IN POLYMERS |
|---|---|---|
| 0.425 | 95.2 | n.d. |
| 0.40 | 93.0 | n.d. |
| 0.375 (n = 2) | 94.2-93.2 | ≥97 |
| 0.35 | 90.8 | ≥97 | n.d.: not determined

The above results demonstrate to at under the best NaCl concentration conditions the reduction in polymer is not lessened by increasing the applied loading up to 50 CV (or 360 mg IgG/ml gel). Likewise it has been established that the range from 0.40 M to 0.35 M of NaCl can be used to obtain a maximum loading capacity with a minimum polymer content (of ≤0.06%-0.31%) and an IgG recovery (monomer/dimer) of between 90.8% and 94.2%.

The best results are obtained at a pH of 4.5, a NaCl concentration of 0.375 M, with a concentration of 10 AU by O.D. (280 nm) and an injection flow of 20 CV/h. it has been shown that the residual polymer is ≤0.06% (duplicate of the test) at 50 CV (360 nm IgG/ml gel) with an IgG recovery of 93.2%-94.2%. The process time did not exceed 3 hours.

Example 7

In order to know the pH range in which a stable NaCl concentration of 0.35 M can be used, and to optimise the elimination of polymers by minimising IgG recovery, a procedure as in Example 4 was used, studying a pH range between 4.5 and 5.0, and samples of the column effluent were obtained at the end of 2 CV, 21-25 CV and 50 CV to determine the protein by O.D. (280 nm) and polymers by HPLC, and to calculate the % protein recovery and polymer reduction. The results are shown in Table 9.

TABLE 9

| COLUMN VOLUME (CV) USED | INJECTED LOADING (mg IgG/ml gel) | POLYMER (%) EFFLUENT AT DIFFERENT pH values | | | |
|---|---|---|---|---|---|
| | | pH 4.96 | pH 4.88 | pH 4.76 | pH 4.50 |
| Initial loading solution | 0 | 2.25 | 1.72 | 1.95 | 1.99 |
| 2 | 14 | 0.45 | 0.20 | 0.17 | ≤0.06 |
| 21-25 | 151-180 | 1.06 | 0.59 | 0.24 | ≤0.06 |
| 50 | 360 | 1.25 | 0.66 | n.d. | ≤0.06 |
| Total loading effluent up to 50 CV | 360 | 1.13 | 0.63 | n.d. | ≤0.06 | n.d.: not determined

Table 10 shows the results of calculating IgG recovery and polymer redaction in the effluent at the final maximum applied loading value (50 CV), and the polymer reduction in the effluent at half the maximum loading (approximate 25 CV).

TABLE 10

| pH | IgG RECOVERY (50 CV) (%) | POLYMER REDUCTION (50 CV) (%) | POLYMER REDUCTION (25 CV) (%) |
|---|---|---|---|
| 4.96 | 96.8 | 49.8 | 52.9 |
| 4.88 | 96.6 | 63.3 | 65.7 |
| 4.76 | 94.3 (*) | n.d. | 87.7 |
| 4.5 | 90.8 | 297 | ≥97 |

(*) Determined in the effluent at 21 CV;
n.d.: not determined

The above results demonstrate the strong dependency between pH and NaCl for effective polymer reduction with minimum IgG loss. At a concentration of 0.35 M of NaCl the most appropriate pH within the range tested was found to be approximately between 4.76 and 4.50, so that the residual polymer was between ≤0.06%-0.24% (applying 21-50 CV) and IgG recovery was between 90.8% and 94.3%. The process time was between 2 and 4 hours.

Example 8

The procedure was the same as in Example 6, but a pH of between 4.85 and 4.88 was established in order to investigate the best NaCl concentration conditions between 0.1 M and 0.4 M. The results are shown in Table 11.

TABLE 11

| COLUMN VOLUME (CV) | INJECTED LOADING (mg IgG/ml gel) | EFFLUENT AT DIFFERENT NaCl CONCENTRATIONS | | | | | | |
|---|---|---|---|---|---|---|---|---|
| | | 0.4M (n = 2) | 0.375M | 0.35M | 0.325M | 0.3M (n = 3) | 0.275M | 0.1M |
| Initial loading solution | 0 | 1.55 2.19 | 1.71 | 1.72 | 1.28 | 1.94 1.33 1.57 | 2.11 | 1.51 |
| 2 | 14 | 0.52 0.56 | 0.25 | 0.20 | 0.06 | ≤0.06 ≤0.06 ≤0.06 | ≤0.06 | ≤0.06 |
| 25 | 180 | 0.98 1.18 | 0.84 | 0.59 | 0.25 | 0.10 0.13 0.12 | ≤0.06 | ≤0.06 |
| 50 | 360 | 1.23 1.34 | 0.94 | 0.66 | 0.25 | 0.13 0.16 0.15 | ≤0.06 | ≤0.06 |
| Loading effluent at 50 CV | 360 | n.d. | 0.87 | 0.63 | 0.17 | ≤0.06 n.d. 0.13 | ≤0.06 | ≤0.06 | n.d.: not determined

Table 12 shows the results of calculating IgG recovery and polymer reduction in the effluent at the final maximum applied loading value (50 CV).

TABLE 12

| NaCl CONCENTRATION (mol/litre) at pH 4.85-4.88 | (%) IgG RECOVERY | (%) POLYMER REDUCTION |
|---|---|---|
| 0.40M | 95-97 | n.d. |
| 0.375M | 96.3 | 49.1 |
| 0.35M | 96.6 | 63.4 |
| 0.325M | 94.9 | 86.7 |
| 0.3M | 93.7 | ≥97 |
|  | 93.6 | n.d. |
|  | 93.7 | 91.7 |
| 0.1M | 76.0 | ≥96 | n.d.: not determined

The above results show that the process is viable at pH 4.85-4.88 within the range from 0.325 M to 0.275 M of NaCl for a maximum loading capacity (50 CV, or 360 mg IgG/ml gel), with a minimum residual polymer content (≤0.06%-0.17%) and IgG recovery (monomer/dimer) of between 92.5% and 04.9%. The best results were obtained with a NaCl concentration of 0.3 M, with which a recovery of 93.7% and a maximum residual polymer of 0.13% in the effluent were achieved. At the lower NaCl concentration of 0.1 M polymers were reduced completely, but IgG recovery was less than 90%.

Comparing the results in this Example 3 and those in Example 6 the strong dependency between pH and NaCl is evident, and these parameters have to be adjusted within an appropriate range to achieve optimum polymer reduction and IgG recovery values. The above examples demonstrate that the desired results as regards residual polymer ≤0.3% and reduction ≥85%, and IgG recovery (monomer/dimer) ≥90% are obtained between pH 4.5 and pH 4.9 with a NaCl concentration of 0.275 M to 0.4 M.

Example 9

The purpose or this test was to evaluate the loading capacity of POROS HS® resins (Applied Biosystems, United States) when using a conventional chromaLegraphy process, which implies adsorption of all the IgG for subsequent elution, followed by comparison of the results obtained with the previous embodiments of the invention. The conventional chromatography process was carried out under conditions for total IgG adsorption to saturation ot the resins, at different injection flows.

Starting from a production lot processed in the same way as in Example 3 as far as obtaining a pasteurised solution, the solution was dilated with some 4 times of 10 mH (millimol/liter) sodium acetate solution at some 20-25° C. in order to provide some 10 AU of optical density (at 280 nm) with approximately 8% (w/w) of sorbitol. The solution was adjusted to pH 4.5 through the addition of dilute HCl (0.1 M-0.5 M).

Injection was into a strong polystyrene synthetic resin cation chromatography column (POROS HS® 50 µm, Applied Biosystems, United States) of some 4 ml volume (height 4 cm and cross-section 1 cm². The column was equilibrated with some 10 column volumes of a 10 mM sodium acetate buffer solution at a pH of 4.5. The product was injected at different loading flows of between 5 and 20 column volumes/hour. Samples of the column effluent were taken from initial injection to different column volumes determining the protein by O.D. (280 nm) in order to calculate the maximum loading capacity under dynamic flow conditions at an approximate protein value of 5% in the injected solution. The results obtained are shown in Table 13.

TABLE 13

| INJECTION FLOW (CV/hour) | LOADING CAPACITY (mg of IgG/ml of gel) |
|---|---|
| 5 | 63 |
| 10 | 58 |
| 20 | 55 |

From the results it is deduced that the maximum, capacity of the resins used for total adsorption of load under the best flow dynamics conditions in a conventional chromatography process is to be found at around 60 mg IgG per ml of resin, and remains virtually unchanged over the injection flows studied of 5-20 CV/h. Given that this result is very far (some 6 times lower) than, the >360 mg IgG/ml of gel obtained in Examples 6 and 8 applying the process oondioions according to this invention, it is demonstrated that the productivity of the process according to this invention is very much superior to that of the conventional chromatography described in the prior art.

Example 10

In this example the test was designed in order to determine the chromatographic resolution (polymer separation) and recovery of IgG under full chromatographic cycle conditions (loading, washing and elution) with total adsorption of the IgG (conventional chromatography), and to compare the results obtained with the previous examples of the process according to the invention.

The procedure was the same as in Example 9, but a starting quantity of IgG solution equivalent to 80% of its maximum capacity (some 50 mg IgG/ml of gel) at a flow of some 5 CV/h was injected into the column. After all the product had been loaded poat-washing was carried out with some 8 CV of buffer solution equal to the initial equilibrated solution comprising 10 nM sodium acetate at pH 4.5. The IgG was subsequently eluted applying a NaCl concentration gradient from 0 to 1 M (mol/liter) containing 0.5 M glycine at pH 4.5 in a total of some 25 CV. The eluted IgG was collected in fractions for subsequent protein analysis (O.D. 280 nm) and analysis of molecular distribution (HPLC). The results are shown in Table 14.

TABLE 14

| FRACTION | VOLUME (CV) | POLYMERS (%) | TOTAL IgG RECOVERY (%) |
|---|---|---|---|
| APPLIED SOLUTION | 14 | 2 | 100 |
| LOADING + POST-WASHING EFFLUENT | 22 | n.d. | n.d. |
| $1^{ST}$ FLUID FRACTION | 16 | ≤0.06 | 64 |
| $2^{ND}$ FLUID FRACTION (TAIL) | 2.5 | 19 | 6 |
| $2^{ND}$ PEAK | 4 | 57 | 16 |
| REGENERATION | 5 | 50 | 4 | n.d.: not determined

In accordance with the above results it has been demonstrated that for a loading of 50 m IgG/ml of gel a maximum recovery of 64% IgG (menoraer/dimer) is obtained for a polymer content ≤0.06%, most of the IgG mixed with unrecoverable polymer being found in the tail fraction and $2^{nd}$ elution peak. This recovery value is not comparable with those obtained in the previous examples in which the process according to this invention is applied, in which satisfactory elimination of polymer and a recovery of more than 90% IgG is demonstrated.

Example 11

An additional test was designed to study the pH limits and ionic strength (NaCl) which could be used and to know the effect of the IgG concentration in the loading.

Various tests were carried out with pasteurised IgG originatino from different production lots processed in the same way as in Example 3. Nevertheless in one of the tests 4-fold dilution (to O.D. 280 nm-10 AU) was used, and the remainder with 1.5-2 times dilutions (to O.D. 280 nm=20-23 AU), approximately, using 10 mM sodium acetate solution, and to each of these the NaCl required to achieve the desired final concentration between 0.275 M and 0.40 M was added, adjusting to a final pH of 4.2 and 5.5 respectively. These pH adjustments were made using dilute acetic acid. The adjusted solutions were injected into a POROS® HS 50 column (Applied Biosystems, United States) in independent cycles as described in Example 4, but in this case using between approximately 150 and 750 mg IgG/ml of gel in the tests performed.

Polymer and dimer content (%) were determined by HPLC and IgG recovery (%) was determined for different loading values. The values obtained are shown in Table 15.

TABLE 15

| pH | [NaCl] (M) | Initial O.D. 280 | Usage (CV) | Loading (mg IgG/ ml gel) | Initial Pol. (%) | Initial Dim. (%) | Final Pol. (%) | IgG Recovery (%) | Polymer reduction (%) |
|---|---|---|---|---|---|---|---|---|---|
| 4.2 | 0.45 | 10 | 32 | 230 | 2.45 | ≤1 | ≤0.06 | 91.0 | ≥98 |
| 5.0 | 0.275 | 23 | 20 | 330 | 2.61 | N.D. | ≤0.06 | n.d. | ≥98 |
|  |  |  | 35 | 580 |  |  | 0.07 | 92.6 | 97 |
| 4.85 | 0.275 | 20.6 | 10 | 147 | 1.76 | 2.5 | ≤0.06 | 92.5 | ≥96 |
|  |  |  | 25 | 369 |  |  | ≤0.06 | 99.5 | ≥96 |
|  |  |  | 40 | 590 |  |  | 0.12 | 97.2 | 93 |
|  |  |  | 50 | 737 |  |  | 0.61 | 96.0 | 65 |
| 5.5 | 0.20 | 22.41 | 2 | 32 | 2.76 | 4.5 | ≤0.06 | 80.1 | ≥98 |
|  |  |  | 25 | 403 |  |  | 0.38 | 96.9 | 86 |
|  |  |  | 50 | 806 |  |  | 1.34 | 94.5 | 51 |

N.D.: not detected
n.d.: not determined

On the basis of different pasteurised lots having an initial polymer content equivalent to and less than 3% it has been demonstrated that for any adjustment value within the limits explored in this example (pH 4.2-5.5 and NaCl 0.20-0.45 M) it is possible to adsorb polymers selectively up to values between ≤0.06%-0.12%, equivalent to reductions of between 93% and ≥98%, and IgG recoveries in excess of 80% (91.0-99.5% achieved between pH 4.2 and 5.0). Likewise it should be pointed out that the loading capacity and efficiency of the column are not diminished as the protein concentration in the product solution increases to a 280 nm O.D. value of 23 AU equivalent to 14.7-16.5 mg of IgG/ml, with loading of 580-590 mg IgG/ml of gel being achieved. However, at the upper end of the pH range (pH 5.5) the salt solution must be appreciably reduced (from 0.45 M to 0.2 M) in order to achieve a significant reduction in polymer. Likewise a smaller loading capacity than at lower pH values is observed, because when 403 mg IgG/ml gel are used a greater polymer content is measured, the reduction in this being only 86%. This effect can be attributed to the presence of a larger quantity of dimer molecules present at pH 5.5, the proportion of which increases with pH, in comparison with pH 4.2.

Example 12

From prior Examples 6, 8 and 11 an empirical iormuia (1) has been determined for POROS®-HS 50 polystyrene perfusion resin from which it is possible to establish with greater precision the NaCl concentration necessary in order to obtain the hoped-for for results for final polymer and recovery as a function of pH used. The expression: (1) [NaCl]=0.24+(5.2−pH)/5=1.28−0.2×pH provides approximately the hoped-for values within the pH range established (pH 4.2-5.5) for the resin studied. On the basis of the data in the examples, for a final polymer preferably ≤0.1% and a recovery of not less than 90% the NaCl concentrations required at different pH (observed value and value calculated according to the formula) are shown in Table 16.

TABLE 16

| pH | Observed value (M) | Calculated value (M) |
|---|---|---|
| 4.20 | 0.45 | 0.44 |
| 4.50 | 0.375 | 0.38 |
| 4.85-4.88 | 0.300-0.275 | 0.31 |
| 4.96 | 0.275 | 0.29 |

TABLE 16-continued

| pH | Observed value (M) | Calculated value (M) |
|---|---|---|
| 5.20 | n.d. | 0.24 |
| 5.50 | 0.20 | 0.18 |

The results in Table 16 show a good linear correlation between the observed values and the values calculated according to the formula, including at extreme pH values.

Example 13

Plasma was processed in the same way as in Example 1 to obtain a purified polyvalent IgG solution (purity ≥97% IgG) by ethanol fractionation (according to the Cohn-Oncley method). The Fr-II obtained was diafiltered through 10 kDa membranes to 60 AU and subsequently pasteurised (10-11 hours at 60-61° C.) in the presence of 33% d-sorbiiol (weight/ weight) and a pH of 5.5±0.5. The pasteurised solution was diluted approximately 4 times with 10 mM sodium acetate solution at pH 4.85 so that the 280 nm O.D. changed from 42.8 AU to 10.7 AU and NaCl was added until a final concentration of 0.275 moles per liter of solution was obtained, adjusting the pH to 4.85 using 0.1 M HCl. The proportion of polymer determined by HPLC was 0.88%. Immediately afterwards this was injected into a column with polystyrene cation exchange resins (50 µm POROS-HS®) and a volume of 8.0 ml (cross-section 0.8 cm²×height of 10 cm) with a flow of approximately some 20 CV/hour. Samples of the column effluent were obtained at different applied loading volumes (CV) and for the final pool, determining tire molecular distribution (high molecular weight polymers) by HPLC ana the reduction obtained. The values found are shown in Table 17.

TABLE 17

| Loading | | | |
|---|---|---|---|
| Loading volumes (CV) | mg IgG/ml gel | Polymer (%) | Polymer reduction (%) |
| 2 | 15 | ≤0.06 | ≥93 |
| 25 | 192 | ≤0.06 | ≥93 |
| 50 | 385 | ≤0.06 | ≥93 |
| Pool | 385 | ≤0.06 | ≥93 |

The results obtained show that with the best adsorption process conditions it is possible to retain all she polymers (up to ≤0.06%) formed in the pasteurisation of IgG previously purified by ethanol fractionation with a high injection loading (385 mg of IgG/ml of resin).

Example 14

This test was designed to determine the viability of the process when different purification steps are incorporated into a single step. It was decided to determine whether polymer adsorption could be combined with a prior optional step of treatment with solvent-detergent and subsequent adsorption of those reagents.

In order to do this Fr-II+III was the starting material and was processed in the same way as in Example 3 to obtain a bulk pasteurised solution. This solution vaas diluted to a 280 nm O.D. of 28±1 AU (approximately 2% of protein) and a concentrated solution (×10 times) of solvent-detergent solution comprising tri-n-butyl phosphate and Triton X-100 were added to achieve final concentrations of 0.3±0.1% and 1.0±0.3% respectively. The solution was raised to 25±2° C. and homogenised for some 30 minutes. It was then transferred to another suitable vessel in order to be incubated for some 6 hours at 25±2° C. After treatment the solution vwas diluted some 10% with 100 mM sodium acerate and 2.75 M NaCl solution so that the final concentrations were 1/10 parts of those added and the protein concentration was 16.5 mg/ml. The pH of the solution was adjusted to 4.85±0.05 with 0.1 M HCl, if necessary, yielding a volume of 167 ml.

Prior to this a column of volume 17.5 ml and height 10 cm of hydrophobic resin (C8 hydrocarbon) and a matrix with silanol groups (SDR-KyperD® by Pall, United States) and another POROS®-HS® cationic resins column (50 µm, Applied Biosystems, United States) of volume 8.0 ml were conditioned. The two columns were connected in series in such a way that the first (SDR-HyperD®) fed the second (POROS-HS®) and these were conditioned by flowing through an equilibrating solution comprising 10 mM sodium acetate, 0.275 M MaCl at a pH of 4.85±0.05 in a flow equivalent to 6 CV/h and 13 CV/h for the first and second columns respectively.

The previously prepared IgG solution (167 ml) was injected into the first SDR-HyperD® column and the effluent from the latter was fed to the second POROS-HS® column. The loading values calculated for each column were: 1) 167 ml/17.5 ml=9.5 CV for the SDR-HyperD® column; 2) 167 ml/8.0 ml=21 CV for the POROS-HS® column. The injection flow throughout the process was 6 and 13 CV/h for the first arad second columns respectively. At the end of loading post-vashing was carried out with some 2 CV of equilibrated solution, collecting all the effluent from the columns in a pool.

The results for molecular distribution (HPLC) and protein (by 280 nm O.D.) for each step are summarized in Table 18.

TABLE 18

| STEP | Polymer (%) | Protein (%) | Recovery (%) |
|---|---|---|---|
| Pasteurised | 2.22 | 2.75 | 100 |
| SD treated | 3.67 | 1.80 | 100 |
| Adjusted | 3.67 | 1.65 | 100 |
| SDR + POROS effluent | ≤0.06 | 1.58 | 95.7 |

The above results show that the polymer adsorption process can be perfectly incorporated and performed simultaneously with other steps of the process, as a result of which the overall time is reduced, together with reagent consumption in prior conditioning and subsequent washing.

Example 15

The polymer retention capacity of different commercially assailable cationic resins was tested to achieve the best possible separation with respect to IgG monomers/dimers. In order to do this resin matrices of different origin were compared, especially acrylic (Toyopearl®) against agarose (Sepharose®). The resins were packed in columns of 1.75 cm² cross-section with a packed height of 100 mm (XK16® from GE-Healthcare) with the resins GigaCap Toyopearl-S 650® and SP-Sepharose XL® each.

The starting material was a mixture of different lots of pasteurised IgG solution treated as in Example 3, to which NaCl was added up to 0.275 M and 0.20 M, adjusting the pH to 4.85±0.05 with 0.1 M HCl if necessary. The solutions had a protein concentration of some 22 AU and up to 50 CV were injected at a flow of some 15 CV/h into columns which had been prepared and conditioned with the same NaCl and pH concentrations as the IgG solution under test.

The polymer recovery results obtained for different column volumes used in comparison with the initial one are show in Table 19.

TABLE 19

| | Loading | | (%) Polymer recovery | |
|---|---|---|---|---|
| Resin | CV | Mg protein/ml gel | NaCl (0.275M) | NaCl (0.200M) |
| GigaCap ToyoPearl-S 650 M | 0 | 0 | 100 | 100 |
| | 10 | 158 | 97 | 15 |
| | 25 | 396 | 100 | 73 |
| | 40 | 638 | 104 | 97 |
| | 50 | 791 | 110 | 110 |
| SP-Sepharose XL | 0 | 0 | 100 | 100 |
| | 10 | 158 | 98 | 89 |
| | 25 | 396 | 100 | 95 |

TABLE 19-continued

| | Loading | | |
|---|---|---|---|
| | Mg protein/ml | (%) Polymer recovery | |
| Resin | CV | gel | NaCl (0.275M) | NaCl (0.200M) |
| | 40 | 633 | 103 | 95 |
| | 50 | 791 | 95 | 91 |

Total protein recovery varied from 98% to 100% for SP-Sepharose XL resin, and from 90 to 100% for GigaCap-S 650M (some 98% at 10 CV and 0.2M NaCl).

The above results show that acrylic cationic resins (of the GigaCap-S® 650M type) like POROS-HS® (cationic polystyrene) are capable of selectively retaining the polymer formed by pasteurisation of IgG with the ability to reduce the polymer present to 85% (15% recovery) for a protein loading of 158 mg/ml of gel and a total protein recovery of 98%. Obviously, the result obtained can be optimised in relation to pH (reducing it), improving the loading capacity to achieve for example some 25 CV (396 mg protein/ml gel).

It has been found that the resins from non-synthetic matrices of the agarose type (Sepharose XL) do not have sufficient resolution capacity to separate polymers from IgG monomers/dimers under the explicit conditions for selective adsorption of the former in the loading offluent.

Likewise it will be seen that the most appropriate pH and NaCl concentration conditions are specific to the type or synthetic perfusion resin used. Thus for a GigaCap-S® 650M type acrylic resin at pH 4.85 not more than 0.2 M of NaCl are required, whereas 0.3 M of NaCl would be required for POROS-HS® 50 μm resin.

It is clear that a person skilled in the art can find the most appropriate relationship between pH and NaCl concentration for each type of synthetic perfusion resin.

Example 16

The scaleability of the process in steps up to the final product formulated and concentrated as IGIV with 10% protein was then checked, examining the compositional characteristics of the product.

A plasma pool of more than 1000 liters was fractionated with ethanol to obtain Fr-II+III and purification was continued until a pasteurised bulk solution was obtained as described in Example 3

6.31 kg of the above pasteurised solution (equivalent to some 26.2 liters of starting plasma), were taken after dilution with water for injection to an optical density of 27.98 AU (280 nm) and a conductivity of 0.26 mS/cm, checking that its pH was 4.65. Some 0.70 kg of concentrated, solution (x 10 times) of 3% tri-n-butyl phosphate and 10% Triton X-100 were added over some 5-10 min with vigorous stirring. The pH was adjusted to 4.79 by the addition of 0.1 M NaOH. 7.04 kg of solution were obtained ana were incubated at ambient temperature (18-25° C.) for up to 6 hours. The tri-n-butylphosphate content was determined by gas chromatography to be 0.28% (2800 ppm).

Subsequently 1.5 M NaCl solution containing 10 mM sodium acetate at pH 4.85 was added to react a final NaCl concentration of 0.275 M. The resulting pH was 4.81. Subsequently 6930.9 g of the solution were obtained and injected into a 140 mm diameter column containing 770 ml of SDR-KyperD® resins (from Pall), the resin height being 50 mm. Injection was carried out at ambient temperature and at an equivalent flow of 6.1 CV/hour, such that all the solution was loaded in less than 2 hours. The resulting total loading ratio was 9 CV (6.93 kg/0.770 L=9.0 CV). Subsequently a post-wash was carried out using 3 CV of 0.275 M NaCl and 10 mM sodium acetate solution at pH 4.85, 6.93 kg of column effluent recovered during injection of the product solution were obtained, the pH being 4.82 and the conductivity 16.75 mS/cm. The tri-n-butylphosphate content was ≤5 ppm determined analytically by gas chromatography.

5.772 kg of the above effluent were taken and injected into a 222 ml column of POROS HS® resins (50 μm), the column diameter being 50 mm and the bed height 113 nm. The solution was injected into the column at ambient temperature with a flow of approximately some 10 CV/hour so that the process lasted some 2.5 hours. All the column effluent obtained during loading the product was collected and combined with 1 CV of post-wash with 0.275 M NaCl, 10 mM sodium acetate and 17% sorbitol (weight/weight) solution at pH 4.85. 5.776 kg of the effluent pool from the column recovered during injection of the product solution were obtained, the optical density being 18.508 AU (280 nm), the pH being 4.84 and the conductivity being 16.95 mS/cm.

The above effluent pool was clarified by filtering through 0.1 μm and was then nanofiltered in series with a pore gradient of 35 nm (Planova® 35N)+20 nm (Planova® 20N). When nanofiltration of the product was complete it was post-washed with a volume equivalent to 5% of the recovered volume of the same post-wash solution usee in the POROS HS® column, the total process time being some 18 hours. The quantity of nanofiltrate obtained was 6.797 kg, the pH was 4.83, the turbidity 2.71 NTU and the conductivity 17.1 nS/cm.

The nanofiltered solution was ultrafiltered through a polyethersulfone membrane having a nominal molecular cut-off 100 kDa. The product was first concentrated 3.3 times, from an optical density of 14.4 AU (280 nm) to approximately 50±10 AU (280 nm), and then it was diafiltered at constant volume with approximately 7 volumes of dialysis solution comprising 2 mM acetic acid adjusted to pH 4.2±0.2 with NaOH. After checking the conductivity (220 μs/cm) a sufficient quantity of concentrated 33% sorbitol solution was added to bring the final sorbitol concentration to approximately 5% (weight/volume). Finally it was concentrated some 3.5 times to achieve an optical density of 140±5 AU (280 nm), equivalent to some 10% of protein, and the pH was adlusted to 5.25±0.25 with 0.1 M NaOH. 552.1 g of solution at a final pH of 5.26, with a turbidity of 5.45 NTU and a conductivity of 1.18 ms/cm were obtained. This solution was filtered through 0.22 μm and dosed into bottles, with the pH being 5.34, the osmolality 330 mOsm/kg, the turbidity 4.62 NTU and the conductivity 1.34 mS/cm. The process time for this step was 9.5 hours.

The metered bottles were held at a 5±3° C. and 25±2° C. for more than 15 days without showing any signs of gelling, or turbidity or sedimentation, changes in colour or the appearance of visible fibres or particles.

Table 20 shows the results for polymers, dimer, monomer and fractions in the different steps of the overall acquisition process.

TABLE 20

| Step of the process | Polymer (%) | Dimer (%) | Monomer (%) | Fractions (%) |
|---|---|---|---|---|
| Pasteurised | 2.0 | 3.2 | 94.8 | 0 |
| SDR effluent | 2.7 | 2.6 | 94.1 | 0.6 |
| POROS effluent | ≤0.06 | 1.9 | 98.1 | 0 |
| Nanofiltrate | ≤0.06 | 3.0 | 96.5 | 0.5 |
| Final concentration (0.2μ) | ≤0.06 | 4.3 | 95.6 | 0.1 |

From the above results it is apparent that control of the dimer content (≤5%), which is achieved as illustrated previously in the prior examples through adjusting pH and salt concentration, in the product before the POROS column (in the Pasteurised and SDR effluent) makes excellent adsorption of the polymer present (≤0.06%) possible, minimising losses of dimer IgG (2.6% in SDR effluent and 1.9% in POROS effluent).

It is concluded that the overall process for obtaining IGIV, by incorporating the step of eliminating aggregates/polymers with the SD treatment and its separation, together with nanofiltration, diafiltration and final formulation is wholly viable and scaleable, excellent values for final product as regards polymer content (≤0.06%) and fractions (0.1%) being obtained.

Example 17

The product obtained (10% IGIV) in Example 16, metered into 10 ml glass bottles at 10 ml per bottle, hermetically sealed, with a 20 mm Ø butyl rubber stopper were stored at ambient temperature (25±5° C.), protected from the light, for 12 months. After a time which was established as being approximately 1 year they were inspected visually (physical appearance) and the parameters most representative of stability were determined analytically. The values obtained at the start (t=0) and end of storage (t=1 year) are shown in Table 21. Likewise the normal values obtained on an industrial scale using the stats of the art (Patent ES-200100101) are also included.

TABLE 21

| PARAMETER | TIME = 0 | TIME = 1 year (T: 20-30° C.) | Specifications (Eur. Ph.) |
|---|---|---|---|
| pH | 5.34 | 5.28 | 4.0-7.4 |
| Turbidity (NTU) | 4.62 | 7.09 | n.e. |
| Conductivity (mS/cm) | 1.34 | 0.63 | n.e. |
| Osmolality (mOs/kg) | 330 | 357 | ≥240 |
| Polymers (% HPLC) | ≤0.06 | 0.27 | ≤3.0 |
| Fragments (% HPLC) | 0.09 | 0.92 | ≤5.0 |
| $IgG_1$ (%) | 67.7 | 67.5 | (equivalent to plasma) |
| $IgG_2$ (%) | 26.2 | 26.2 | (equivalent to plasma) |
| $IgG_3$ (%) | 3.3 | 3.1 | (equivalent to plasma) |
| $IgG_4$ (%) | 2.7 | 2.6 | (equivalent to plasma) |
| PKA (UI/ml) | <2 | <2 | ≤25 |
| ACA ($CR_{20}$/mg) | 0.79 | 0.89 | ≤1 | n.e.: not established;
Eur. Ph.: European Pharmacopoeia

As far as visual appearance is concerned, there was found to be no deterioration in the samples both as a result of the presence of particles (fibres, clots or sediments), or turbidity (transparent) or colouration (colourless). It is concluded that the product obtained was stored essentially unchanged (polymers, enzymes such as PKA, ACA, etc.) for 1 year at an ambient temperature of 25±5° C., the product complying with the values stated in the European Pharmacopoeia (Eur.Ph.).

Example 18

One lot was processed at a preparation scale size equivalent to Example 16 with only one change in the order of the sequence of viral inactivatlon steps, such that treatment with SD was carried out on the initial diafiltered material and then these reagents were adsorbed with SDR-HyperD® resins, and then the rest of the process steps required to obtain the product according to the invention, that is pasteurisation in the presence of sorbitol and the capture of molecular aggregates using POROS HS perfusion resins, were performed fn the same way as in Example 16. Finally, the product obtained, stabilised with 5% sorbitol, was raised to the 10% protein concentration of IGIV, sterilised by filtration and metered into 20 ml glass bottles. The bottles hermetically sealed with a butyl rubber stopper were stored fn a cold chamber at 5±3° C. for approximately 1 year and then the most significant parameters for stability, including visual inspection, were determined. The results obtained at the start (t=0) and after storage (t=approximately 1 year), together with the Eur.Ph. specifications are shown in Table 22.

TABLE 22

| PARAMETER | TIME = 0 | TIME = 1 year (T: 2-8° C.) | Specifications (Eur. Ph.) |
|---|---|---|---|
| pH | 5.23 | 5.18 | 4.0-7.4 |
| Turbidity (NTU) | 7.6 | 6.0 | n.e. |
| Conductivity (mS/cm) | 1.45 | 0.64 | n.e. |
| Osmolality (mOs/kg) | 384 | 399 | ≥240 |
| Polymers (% HPLC) | 0.30 | 0.40 | ≤3.0 |
| Fragments (% HPLC) | 0 | 0.32 | ≤5.0 |
| $IgG_1$ (%) | 67.6 | 70.2 | (equivalent to plasma) |
| $IgG_2$ (%) | 25.4 | 26.9 | (equivalent to plasma) |
| $IgG_3$ (%) | 4.2 | 4.0 | (equivalent to plasma) |
| $IgG_4$ (%) | 2.8 | 3.2 | (equivalent to plasma) |
| PKA (UI/ml) | <2 | <2 | ≤25 |
| ACA ($CR_{20}$/mg) | 0.64 | 0.85 | ≤1 | n.e.: not established;
Eur. Ph.: European Pharmacopoeia

As far as visual physical appearance is concerned it was found that there had been no deterioration in the samples through the presence of particles (fibres, clots or sediments), or turbidity (transparent) or colouration (colourless). The product obtained was stored essentially unchanged (e.g. polymers/fragments and proteolytic enzymes such as PKA) for more than approximately 1 year at a temperature of 5±3° C., the product complying with the values specified in the European Pharmacopoeia (Eur.Ph.).

The invention claimed is:

1. A process for obtaining a liquid IgG composition from an IgG solution partly purified from human plasma, comprising the steps of:
    a) diafiltering the partly purified IgG solution;
    b) stabilising the solution obtained in step a);
    c) heat treating the solution obtained in step b) whereby no more than 3% high molecular weigh aggregates and polymers are generated;
    d) selectively adsorbing at least 85% of the high molecular weight aggregates and polymers in step c) by cation exchange chromatography; and
    e) diafiltering the solution obtained in step d), whereby the liquid IgG composition is obtained , wherein the liquid IgG composition is stable for at least 1 year at a temperature of 2-30° C. and a pH of 4.6-5.8.

2. The process according to claim 1, wherein the partly purified IgG solution has an IgG content of more than 95% in relation to total proteins.

3. The process according to claim 1, wherein the partly purified IgG solution has an IgG content of more than 97% in relation to total proteins.

4. The process according to claim 1, wherein the diafiltration step a) is carried out until the resulting solution has an ethanol concentration of less than 0.5% (weight/volume).

5. The process according to claim 1, wherein the diafiltration step a) is carried out until the concentration of non-denatured precipitation reagents in the resulting solution does not give rise to more than 3% (weight/weight) of the polymers after step c).

6. The process according to claim 1, wherein the diafiltration step a) is carried out until the resulting solution has an ionic strength of less than 1 mS/cm.

7. The process according to claim 1, wherein the pH value at the end of step a) is within the range from 4.2 to 6.0.

8. The process according to claim 1, wherein the diafiltration step a) is carried out with water for injection or with a buffer solution of low ionic strength.

9. The process according to claim 8, wherein the buffer solution of low ionic strength is a ≤5mM solution of acetic acid or sodium acetate, having a pH between 4.0 and 5.0.

10. The process according to claim 8, wherein the diafiltration step a) is carried out in tangential flow mode across membranes having a molecular cut-off between 10 kDa and 100 kDa.

11. The process according to claim 8, wherein in the diafiltration step a) proteins in the human plasma are concentrated to a concentration not exceeding 5% (weight/volume).

12. The process according to claim 1, wherein sorbitol is used as a stabilising agent in the stabilisation step b).

13. The process according to claim 12, wherein the concentration of sorbitol used in the stabilisation step b) is less than 50% (weight/weight).

14. The process according to claim 12, wherein the pH is adjusted to between 4.6 and 5.2 in the stabilisation step b).

15. The process according to claim 1, wherein the heat treatment step c) is carried out at a temperature between 55° C. and 63° C., for a time of between 1 and 24 hours.

16. The process according to claim 15, wherein the heat treatment step c) is carried out at a temperature of 60±1° C., for 10-11 hours.

17. The process according to claim 1, wherein the selective adsorption step d) is carried out in a strong cation exchange chromatography column.

18. The process according to claim 17, wherein the strong cation exchange resin comprises at least one of the cationic sulfone groups covalently bonded to an insoluble synthetic perfusion matrix comprising polymethacrylate or polystyrene whose particle size varies between 20 and 100 μm.

19. The process according to claim 17, wherein in the selective adsorption step d) is carried out with an injection flow of 5-30 column volumes/hour.

20. The process according to claim 1, wherein sodium chloride is added to the solution heat treated in step c) up to a final concentration of between 0.2 and 0.5 M (mol/liter).

21. The process according to claim 20, wherein after the addition of sodium chloride the pH of the solution in step c) is adjusted to between 4.2 and 5.5.

22. The process according to claim 17, wherein in the selective adsorption step d) between 1 and 10 liters of resin are used for each kg of IgG (dry) requiring purification, which is equivalent to a loading of between 100 and 1000 mg of IgG/ml of resin.

23. The process according to claim 22, wherein in the selective adsorption step d) elution is carried out using a decreasing saline gradient.

24. The process according to claim 1, further comprising at least one viral inactivation/elimination treatment step.

25. The process according to claim 1, wherein the diafiltration step e) is carried out with water for injection or with a buffer solution of low ionic strength.

26. The process according to claim 1, wherein in the diafiltration step e) stabilisers for the IgG composition are added.

27. The process according to claim 1, wherein the diafiltration step e) is carried out in the tangential flow mode through membranes having a molecular cut-off between 10 kDa and 100 kDa.

28. The process according to claim 1, wherein in the diafiltration step e) proteins in the solution obtained in step d) are concentrated to a value of between 5% and 22% (w/v).

* * * * *